United States Patent [19]
Fujiwara

[11] Patent Number: 5,878,106
[45] Date of Patent: Mar. 2, 1999

[54] X-RAY DIFFRACTOMETER

[75] Inventor: Tadayuki Fujiwara, Tokyo, Japan

[73] Assignee: Shimadzu Corporation, Kyoto, Japan

[21] Appl. No.: 654,920

[22] Filed: May 29, 1996

[30] Foreign Application Priority Data

May 30, 1995 [JP] Japan ................................. 7-131728

[51] Int. Cl.⁶ .............................................. G01N 23/20
[52] U.S. Cl. ............................................ 378/79; 378/73
[58] Field of Search ....................................... 378/79–81

[56] References Cited

U.S. PATENT DOCUMENTS 5,128,976  7/1992  Moulai ....................................... 378/79

*Primary Examiner*—Craig E. Church
*Attorney, Agent, or Firm*—Nikaido, Marmelstein, Murray & Oram LLP

[57] ABSTRACT

In an x-ray diffractometer having (i) first and second motors 10, 17 for respectively rotating a sample 4 and an x-ray detector 13 around a rotational axis 7 and (ii) θ-2θ interlock control means 22 for supplying drive signals to the motors 10, 17, such that a θ-2θ relationship is always maintained between the angles of the sample 4 and the x-ray detector 13 with respect to irradiated x-rays 2, there is disposed a rotational vibration control unit 23 for supplying, to the first motor for rotating the sample holding member 6, a drive signal for rotationally vibrating the sample, in addition to the drive signal for θ-2θ interlock. Eliminating an individual drive mechanism for rotationally vibrating the sample 4, this arrangement makes it possible that, with a simple and economical structure, diffracted x-rays are efficiently detected even for a sample having an uneven surface, thereby to obtain an accurate measurement result.

6 Claims, 4 Drawing Sheets

X-RAY DIFFRACTOMETER

BACKGROUND OF THE INVENTION

The present invention relates to an x-ray diffractometer for measuring the x-ray diffraction pattern of a polycrystalline sample, a powder sample or the like.

In a qualitative or quantitative analysis of a powder sample or the like, or in an analysis of a crystalline structure, there is generally used a so-called goniometer method in which, while an x-ray beam having a suitable angle of aperture is irradiated to a sample placed at the center of a goniometer and an x-ray detector is rotated around the sample, there is measured the intensity of x-rays diffracted by the sample. In such a goniometer method, there is generally used a so-called θ-2θ interlock scan method in which, when the angle of the sample with respect to a zero angle direction in which the x-ray generator and the goniometer center (i.e., the sample center) are connected to each other, is defined as θ, the sample and the x-ray detector are interlockingly scanned around the same rotational axis such that the angle of the x-ray detector with respect to the zero angle direction is always maintained at 2θ.

According to the θ-2θ interlock scan method, an analysis result with high precision can be obtained by a simple operation for a homogeneous sample. However, for an insufficiently mixed sample, a powder sample in which individual crystalline grains are large, a sample having an uneven surface such as metal in which crystalline grains are coarse due to heat treatment, or the like, the intensity of x-ray deffracted measured by an x-ray detector is reduced, according to the reduction in the number of crystalline grains which contribute to the generation of diffracted rays in one direction; so that this θ-2θ interlock scan method is disadvantageously liable to contain errors in the measurement result.

To solve such a problem, there has conventionally been proposed a sample vibration-type x-ray diffractometer in which, during the θ-2θ interlock scan, the sample is rotationally vibrated (swung), on the same axis as the rotational axis for the θ scan, at an angular speed greater than the scan speed, thereby to increase the number of crystalline grains which contribute to the generation of diffracted rays at each angular position of the sample.

FIG. 5 shows an example of a conventional sample vibration-type x-ray diffractometer of the type above-mentioned. X-rays 52 generated by an x-ray tube 51 are irradiated, as suitably limited in diffusion by a divergence slit 53, to a sample 54 obtained by hardening a powder sample in the form of a plate.

The sample 54 as supported by a sample placing stand 55, is placed on a sample table 56. The sample table 56 is arranged to be rotated around a rotational axis 57 by a motor (not shown) such that the angle θ of the sample 54 with respect to the irradiated x-rays 52 varies with the passage of time. This operation is hereinafter referred to as θ-scan.

X-rays 58 diffracted by the sample 54, are to be detected by an x-ray detector 60 through a detecting slit 59. The detecting slit 59 and the x-ray detector 60 are to be rotated also around the rotational axis 57 by a motor (not shown), and the rotational position is controlled such that the angle of the x-ray detector 60 with respect to the irradiated x-rays 52 is always twice the angle θ of the sample 54 with respect to the x-rays 52, the angle θ varying from time to time. More specifically, in association with the θ scan of the sample 54, the detecting slit 59 and the x-ray detector 60 are scanned at an angular speed which is double the angular speed in the θ scan (hereinafter referred to as 2θ scan).

In addition to the θ scan by the rotation of the sample table 56, the sample 54 is subjected to rotational vibration around the rotational axis 57 by the following mechanism.

The sample placing stand 55 for supporting the sample 54, is supported by the sample table 56 in a manner rotatable around the rotational axis 57 and has, in a unitary structure, a lever 61. On the other hand, a motor 63 having the output shaft to which an eccentric cam 62 is secured, is mounted on the sample table 56, and the lever 61 of the sample placing stand 55 is biased by a spring 64, causing the lever 61 to be normally brought in close contact with the outer peripheral surface of the eccentric cam 62. The motor 63 is rotationally driven at an angular speed greater than that of the motor for rotating the sample table 56 such that the sample 54 is subjected to the θ scan. The rotation of the motor 63 causes the sample placing stand 55 to be rotationally vibrated on the sample table 56 around the rotational axis 57 as shown by the arrow in FIG. 5. Thus, the sample 54 is subjected not only to the θ scan, but also to a rotational vibration at an angular speed faster than that for the θ scan.

According to such a sample vibration-type x-ray diffractometer of prior art, it is required to dispose, on the sample table, a drive mechanism for rotationally vibrating a sample, in addition to the drive mechanism for θ-2θ interlock scan. However, the sample holding members such as the sample table and the sample placing stand are generally replaced according to the shape and type of a sample. Accordingly, it is required in such a conventional diffractometer to mount a drive mechanism for rotationally vibrating a sample on each of all the sample tables to be used. This increases the cost of a sample table. Further, it is rather difficult to install such a drive mechanism for rotational vibration in a limited space on the sample table.

OBJECTS AND SUMMARY OF THE INVENTION

It is an object of the present invention to provide an x-ray diffractometer which can rotationally vibrate a sample without another drive mechanism disposed in addition to a drive mechanism for θ-2θ interlock scan, thus eliminating the need of individually mounting a drive mechanism for rotationally vibrating a sample on a sample holding member to be replaced according to the shape and type of a sample to be used, and which can therefore obtain, without any increase in cost, an excellent x-ray diffraction intensity even for a sample having relatively great crystalline grains.

To achieve the object above-mentioned, the present invention provides an x-ray diffractometer having: a first motor for rotating a rotatable shaft, around the axis thereof, on which mounted is a sample holding member for holding a sample; an x-ray generator for irradiating x-rays to a sample held by the sample holding member; a second motor for rotating, around the axis of the rotatable shaft, an x-ray detector for detecting x-rays diffracted by the sample; and θ-2θ interlock control means for controlling the rotational amounts of the first and second motors such that the rotational amount of the x-ray detector is maintained at twice the rotational amount of the sample holding member, and this x-ray diffractometer is characterized by comprising rotational vibration control means for supplying, to the first motor, a drive signal for rotationally vibrating the sample holding member around the rotatable shaft within a preset angular range, the drive signal being supplied to the first motor in addition to a drive signal supplied from the θ-2θ interlock control means.

According to the x-ray diffractometer having the arrangement above-mentioned, both the drive signal for θ-2θ interlock scan of a sample and the drive signal for rotational vibration of the sample, are supplied to the first motor for rotating the rotatable shaft on which the sample holding member is mounted. As a result, a single rotatable shaft and a single motor (the first motor) for rotating the rotatable shaft give, to the sample, both a motion for θ-2θ interlock scan and rotational vibration. This eliminates the need of disposing, at the sample holding member mounted on the rotational shaft, a drive mechanism for rotational vibration of a sample. Accordingly, an optional sample holding member may be used according to the shape and type of a sample as far as the sample holding member can be mounted on the rotatable shaft, and the sample can be scanned, in association with the x-ray detector, while being rotationally vibrated. It is therefore possible to detect diffracted x-rays with excellent intensity even for a sample having relatively great crystalline grains.

According to a preferred embodiment of the present invention, a step motor is used as each of the first and second motors. In this case, the first motor is arranged to receive both a drive pulse from the θ-2θ interlock control means and a pulse from the rotational vibration control means.

When such a step motor is used, the θ-2θ interlock control means and the rotational vibration control means may be formed by first and second drivers for respectively driving the first and second motors, and a computer for controlling the drivers. The first and second motors may be controlled substantially by a software.

According to the present invention, the θ-2θ interlock control means may be arranged to intermittently supply drive signals to the first and second motors such that the sample holding member and the x-ray detector are scanned stepwise by preset angles respectively, or to continuously supply drive signals to the first and second motors such that the sample holding member and the x-ray detector are continuously scanned at preset angular speeds respectively, or the θ-2θ interlock control means may be arranged to select either the stepwise scan or the continuous scan.

According to the stepwise or continuous manner in which the sample holding member and the x-ray detector are scanned by the θ-2θ interlock control means, the timing at which the rotational vibration control means supplies the drive signal, should be determined as follows. That is, when the scan by the θ-2θ interlock control means is conducted stepwise, the drive signal for rotational vibration is supplied while the sample holding member is stopped. When the scan by the θ-2θ interlock control means is conducted continuously, the drive signal for rotational vibration is supplied such that the sample holding member is rotationally vibrated at an angular speed faster than the angular speed at which the sample holding member is scanned by the drive signal for θ-2θ interlock control, and both drive signals are supplied, as superimposed on each other, to the first motor.

DESCRIPTION OF PREFERRED EMBODIMENTS

The following description will discuss a preferred embodiment of the present invention with reference to attached drawings.

Figure 1:
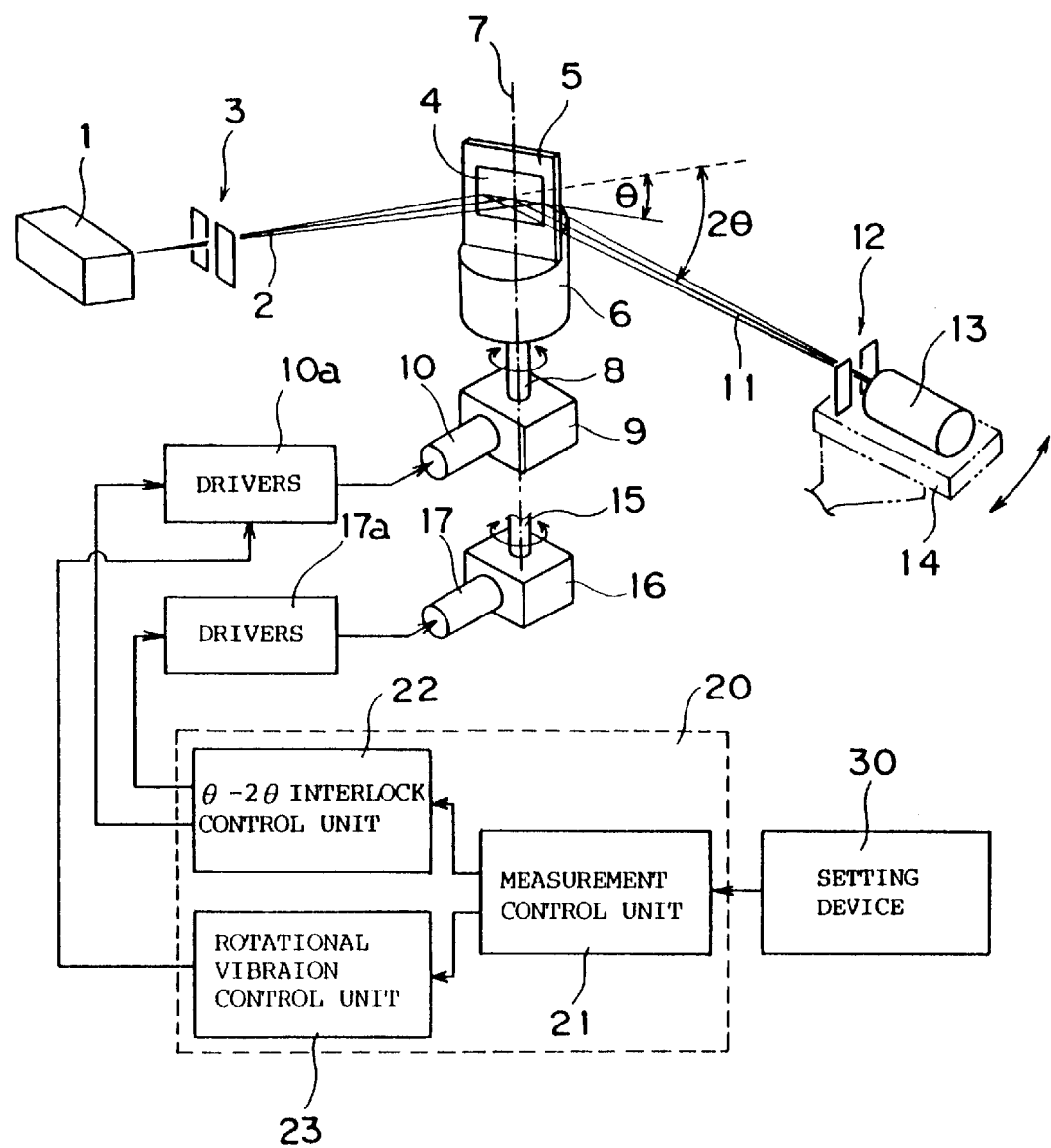
FIG. 1 is a schematic view illustrating the arrangement of an embodiment of the present invention.

FIG. 1 schematically illustrates the arrangement of an embodiment of the present invention. X-rays 2 generated by an x-ray tube 1 are irradiated, as suitably limited in diffusion by a divergence slit 3, to a sample 4. For example, the sample 4 is made by hardening a powder sample in the form of a plate, and held by a sample holding member 6 housed within the frame of a sample holder 5.

The sample holding member 6 is mounted on a rotatable shaft 8 coaxial with a rotational axis 7 of a goniometer. The rotatable shaft 8 is rotatable around the rotational axis 7 by a first motor 10 through a transmission mechanism 9 using a worm gear and the like.

X-rays 11 diffracted by the sample 4 are to be detected, through a detecting slit 12, by an x-ray detector 13 comprising a scintillation detector or the like. A support body 14 which supports the detecting slit 12 and the x-ray detector 13, is mounted, through an arm or the like (not shown), on a rotatable shaft 15 coaxial with the rotational axis 7. This rotatable shaft 15 is also rotatable around the rotational axis 7 by a second motor 17 through a transmission mechanism 16 using a worm gear and the like.

Each of the first and second motors 10, 17 is a step motor and is to be rotationally controlled by each of drive pulses supplied from corresponding drivers 10a, 17a. These drivers 10a, 17a are to be controlled by control signals supplied from a control system 20.

Actually, the control system 20 comprises, as a main body, a computer and its peripheral devices, sequencer and the like, but is shown, in FIG. 1, in the form of a block diagram per main function.

A setting device 30 for setting the measuring conditions, is connected to the control system 20. By this setting device 30, there are set, prior to measurement, the measuring conditions including the scan ranges of the sample 4 and the x-ray detector 13, selection in scan method of either stepwise scan or continuous scan, the step angle in the case of stepwise scan, selection of whether or not the sample 4 is to be rotationally vibrated, the angular range and speed in the case of rotational vibration, the tube voltage and tube current of the x-ray tube 1, integration time during which the x-ray intensity is counted, and the like. The measuring conditions may be set by the setting device 30 at each measurement. Or, the measuring conditions may be set by calling a desired combination from a variety of combinations of measuring conditions previously stored in the memory such as a hard disk or the like.

In the control system 20, a measurement control unit 21 is arranged to control the operation of the whole diffractometer according to the set measuring conditions and to latch, from time to time, a detection output from the x-ray detector 13 through an amplifier, a counter circuit and the like.

A θ-2θ interlock control unit 22 is arranged to supply, according to an instruction from the measurement control unit 21, a control signal such that the rotatable shafts 8, 15 are rotated while always maintaining the θ-2θ relationship between the angles of the sample 4 and the x-ray detector 13 with respect to the irradiated x-rays 2, this control signal being supplied to the drivers 10a, 17a of the first and second motors 10, 17.

A rotational vibration control unit 23 is arranged to supply, according to an instruction from the measurement control unit 21, a control signal such that the sample 4 is rotationally vibrated at the preset angle and speed, this control signal being supplied to the driver 10a of the first motor 10.

Figure 2:
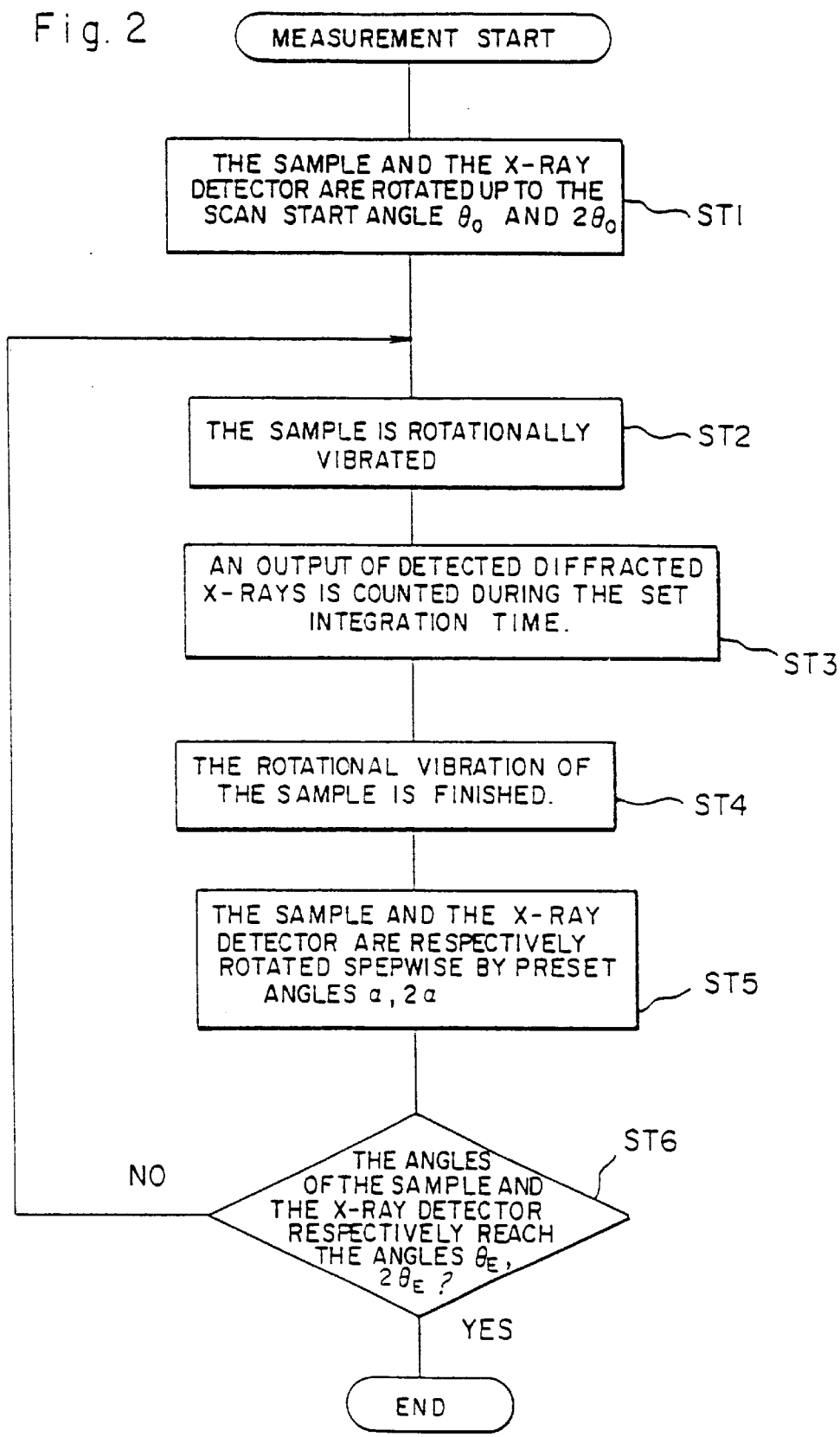
FIG. 2 is a flow chart illustrating an example of the operational procedure of the embodiment in FIG. 1.

With reference to the flow chart in FIG. 2, the following description will discuss an example of the operation of the embodiment having the arrangement above-mentioned. The flow chart in FIG. 2 shows the operation in which the sample 4 and the x-ray detector 13 are scanned stepwise and the sample 4 is rotationally vibrated.

After the measuring conditions have been set, when a measurement start instruction is given, for example, by pressing a measurement start button or the like, the tube voltage and tube current of the x-ray tube 1 are set according to the measuring conditions, and the first and second motors 10, 17 are rotationally driven according to control instructions from the θ-2θ interlock control unit 22 such that the sample 4 and the x-ray detector 13 are rotated up to the scan start angles $\theta_0$ and $2\theta_0$, respectively (ST1). Then, according to a control instruction supplied from the rotational vibration control unit 23 to the driver 10a, the sample 4 is rotationally vibrated within a predetermined angular range β and at a predetermined speed (ST2). This rotational vibration is conducted around the current angle of the sample 4 with respect to the irradiated x-rays 52, this current angle being determined according to the instruction from the θ-2θ interlock control unit 22. In such a state, an output from the x-ray detector 13, i.e., an output of detected diffracted x-rays, is counted during the set integration time (ST3).

Here, the speed at which the sample 4 is rotationally vibrated, is set to such an extent that the sample 4 is vibrated at least once for the integration time during which the diffracted x-rays are measured. The effect of averaging the sample grains by correcting the roughness thereof, is greater with an increase in rotational vibration speed. Accordingly, the speed at which the sample 4 is rotationally vibrated, is preferably faster. On the other hand, the averaging effect becomes greater as the angular range β of rotational vibration becomes greater. However, when the sample is rotated, the sample surface is rotated to change the focal circle in size. This changes the optical concentration condition of x-rays to produce the effect of attenuating x-rays actually incident upon the x-ray detector 13 after having passed through the detecting slit 12. Accordingly, the angular range cannot excessively be increased. It is therefore preferable to set the actual angular range β of rotational vibration to about ±3° in view of the averaging effect and the attenuation effect of incident x-rays due to changes in concentration conditions.

When the counting of diffracted x-rays with the sample 4 rotationally vibrated is finished, the rotational vibration of the sample 4 is finished (ST4). Based on the control instructions supplied to the drivers 10a, 17a from the θ-2θ interlock control unit 22, the sample 4 and the x-ray detector 13 are respectively rotated stepwise by preset angles α, 2α (ST5). Upon completion of such rotation, the sequence is returned to ST2 and the operations from rotational vibration to counting the diffracted x-rays are again executed. These operations are repeated until the angles of the sample 4 and the x-ray detector 13 respectively reach the predetermined scan completion angles $\theta_E$, $2\theta_E$ (ST6).

Figure 3:
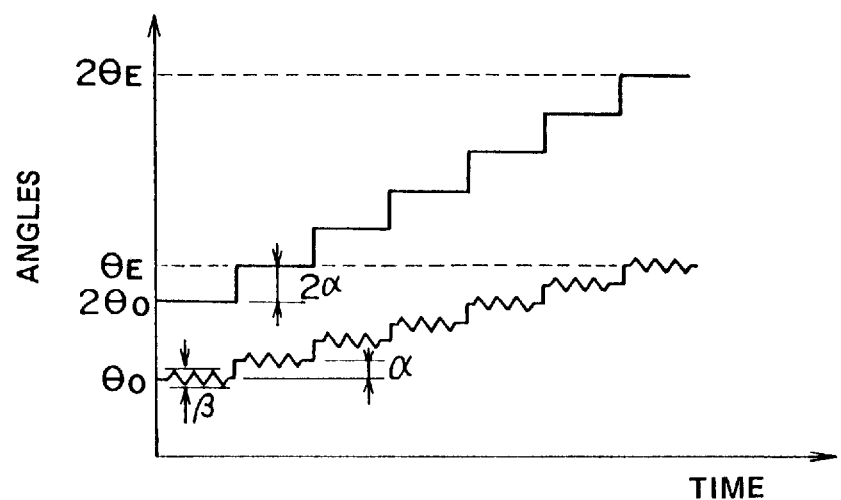
FIG. 3 is a time chart schematically illustrating the changes with the passage of time in the angles of the sample and the x-ray detector with respect to irradiated x-rays where a stepwise scan is selected in the embodiment of the present invention.

FIG. 3 is a time chart illustrating the changes with the passage of time in the angles of the sample 4 and the x-ray detector 13 with respect to irradiated x-rays 2 during the measurement operations above-mentioned. As shown in FIG. 3, the sample 4 and the x-ray detector 13 are respectively scanned stepwise by the set angles α, 2α while always maintaining the θ-2θ relationship between the angles of the sample 4 and the x-ray detector 13 with respect to the irradiated x-rays 2, and a rotational vibration within the set angular range β is given to the sample 4 at each stepwise stop position.

Figure 4:
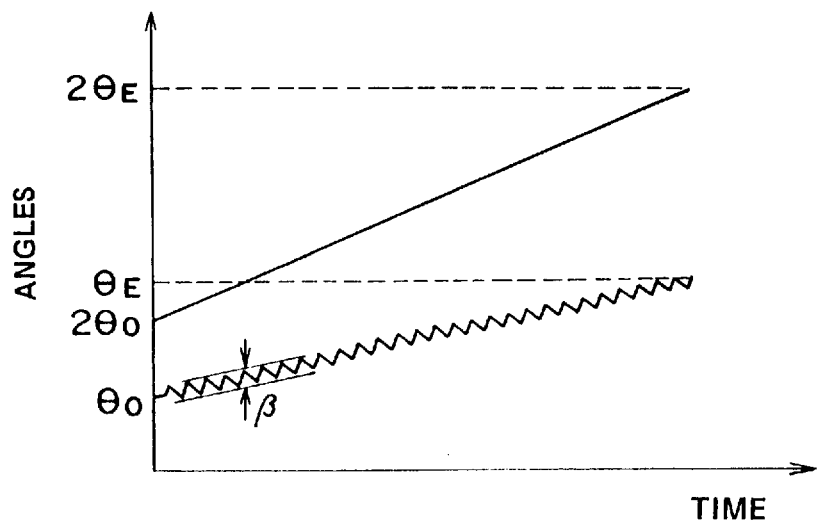
FIG. 4 is a time chart schematically illustrating the changes with the passage of time in the angles of the sample and the x-ray detector with respect to irradiated x-rays where a continuous scan is selected in the embodiment of the present invention.
Figure 5:
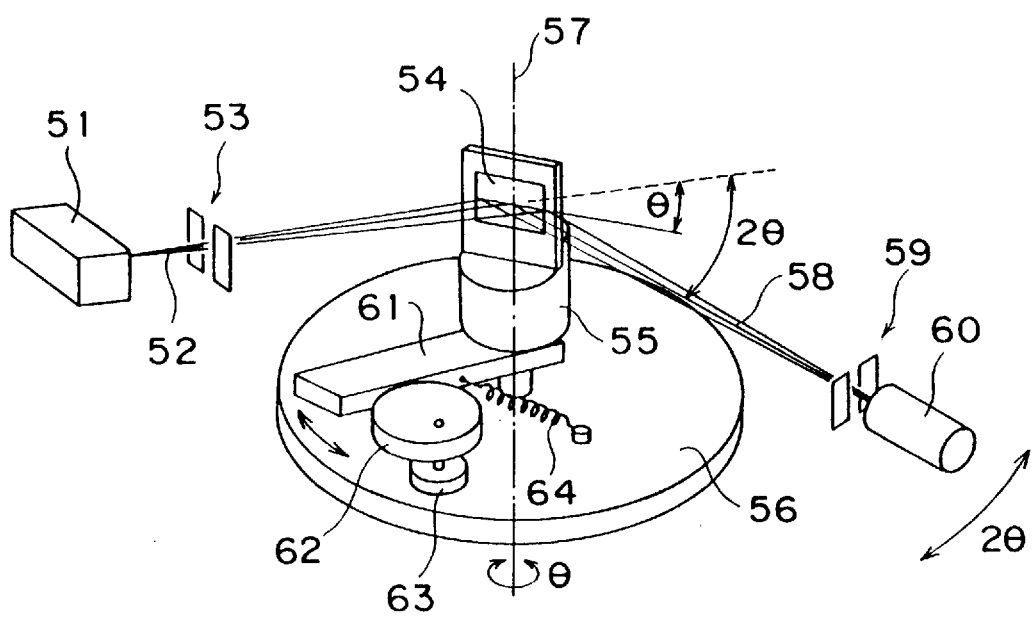
FIG. 5 is a perspective view of an example of the arrangement of a sample vibration-type x-ray diffractometer of prior art.

On the other hand, when the sample 4 and the x-ray detector 13 are continuously scanned, the drivers 10a, 17a continuously supply drive pulses in predetermined cycles to the first and second motors 10, 17 according to instructions from the θ-2θ interlock control unit 22. Accordingly, the sample 4 and the x-ray detector 13 are continuously rotated from the scan start angles $\theta_0$, $2\theta_0$ to the scan completion angles $\theta_E$, $2\theta_E$. At the same time, according to an instruction from the rotational vibration control unit 23, the driver 10a supplies, to the first motor 10, a drive pulse for rotational vibration as superimposed on the drive pulse for θ-2θ interlock. At this time, it is required that the rotational vibration speed of the sample 4 is sufficiently fast as compared with the interlock scan speed of the sample 4. In this continuous scan, the changes with the passage of time in the angles of the sample 4 and the x-ray detector 13 with respect to the irradiated x-rays 2, are as shown in the time chart in FIG. 4.

It is noted that each of the transmission mechanisms 9, 16 for transmitting the rotations of the first and second motors 10, 17 to the rotatable shafts 8, 15, is not particularly limited to a mechanism using a warm gear. It is a matter of course that examples of such a transmission mechanism include, among others, a mechanism in which the x-ray detector 13 is placed on a disk rotatable around the rotational axis 7 and the outer peripheral surface of the disk is rotationally driven by a motor.

I claim:

1. In an x-ray diffractometer having: a first motor for rotating a rotatable shaft on which is mounted a sample holding member for holding a sample; an x-ray generator for irradiating x-rays to a sample held by the sample holding member; a second motor for rotating, around a rotational axis identical with that of the rotatable shaft, an x-ray detector for detecting x-rays diffracted by the sample; and θ-2θ interlock control means for controlling the rotational amounts of the first and second motors such that the rotational amount of the x-ray detector is maintained at twice the rotational amount of the sample holding member, said x-ray diffractometer comprising rotational vibration control means for supplying, to said first motor, a drive signal for rotationally vibrating said sample holding member around said rotatable shaft within a preset angular range, said drive signal being supplied in addition to a drive signal supplied to said first motor from said θ-2θ interlock control means, wherein said first motor provides a motion for θ-2θ interlock scanning and rotational vibration, and wherein an axis for a θ rotational scan is identical with an axis of the rotational vibration.

2. An x-ray diffractometer according to claim 1, wherein each of said first and second motors is a step motor, and said first motor is arranged to receive both a drive pulse from said θ-2θ interlock control means and a drive pulse from said rotational vibration control means.

3. An x-ray diffractometer according to claim 2, wherein said θ-2θ interlock control means and said rotational vibration control means are formed by first and second drivers for respectively driving said first and second motors, and a computer containing a software for controlling said drivers.

4. An x-ray diffractometer according to any of claims 1, 2, or 3 wherein said θ-2θ interlock control means is configured to intermittently supply drive signals to said first and second motors such that said sample holding member and said x-ray detector are scanned stepwise by preset angles respectively, and said rotational vibration control means is configured to supply said drive signal for rotational vibration while said first motor is not being operated.

5. An x-ray diffractometer according to any of claims 1, 2, or 3 wherein said θ-2θ interlock control means is configured to supply drive signals such that said sample holding member and said x-ray detector are continuously scanned at preset angular speeds, respectively, and said rotational vibration control means is configured to superimpose said drive signal for rotational vibration on a continuous drive signal for θ-2θ interlock to be supplied to said first motor.

6. An x-ray diffractometer according to any of claims 1, 2, or 3 wherein said θ-2θ interlock control means is configured to select either the state where said sample holding member and said x-ray detector are scanned stepwise, or the state where said sample holding member and said x-ray detector are continuously scanned, and said rotational vibration control means is configured to operate according to the state selected by said θ-2θ interlock control means such that, when said stepwise scan is selected, said rotational vibration control means supplies said drive signal for rotational vibration to said first motor while the same is not being operated, and that, when said continuous scan is selected, said rotational vibration control means superimposes said drive signal for rotational vibration on said drive signal for θ-2θ interlock supplied to said first motor.

* * * * *